United States Patent
Benson et al.

(10) Patent No.: US 12,372,481 B2
(45) Date of Patent: Jul. 29, 2025

(54) METHODS AND APPARATUS FOR RADIOGRAPHIC SOURCE EXPOSURE

(71) Applicant: QSA Global Inc., Burlington, MA (US)

(72) Inventors: Paul Benson, Waltham, MA (US); Joseph Ryan Lapinskas, Windham, NH (US); David Wood, Waltham, MA (US)

(73) Assignee: QSA GLOBAL INC., Burlington, MA (US)

( * ) Notice: Subject to any disclaimer, the term of this patent is extended or adjusted under 35 U.S.C. 154(b) by 181 days.

(21) Appl. No.: 18/295,626

(22) Filed: Apr. 4, 2023

(65) Prior Publication Data

US 2024/0003833 A1   Jan. 4, 2024

Related U.S. Application Data

(60) Provisional application No. 63/327,544, filed on Apr. 5, 2022.

(51) Int. Cl.
  *G01N 23/06*   (2018.01)
(52) U.S. Cl.
  CPC ......... *G01N 23/06* (2013.01); *G01N 2223/20* (2013.01)
(58) Field of Classification Search
  CPC .... G01N 23/06; G01N 2223/20; G21F 5/015; G21F 5/02; A61B 6/107
  See application file for complete search history.

(56) References Cited

U.S. PATENT DOCUMENTS

| 4,314,157 A | 2/1982 | Gaines |
| 10,276,272 B2 | 4/2019 | Benson et al. |

FOREIGN PATENT DOCUMENTS

| EP | 0513512 | 11/1992 |

OTHER PUBLICATIONS

Int'l Search Report and Written Opinion Appln No. PCT/US2023/065359 mailed Aug. 21, 2023.
QSA Global 880 Series Gamma-Ray Source Projector & Transport Container Operations & Maintenance Manual. MAN-027, Sep. 2022, pp. 1-88.

*Primary Examiner* — Jurie Yun
(74) *Attorney, Agent, or Firm* — McAndrews, Held & Malloy, Ltd.

(57) ABSTRACT

Disclosed example radiographic source exposure devices include: a radiographic source capsule having a radionuclide; a radiographic shield; a channel within the radiographic shield, the channel having a first end and a second end; and a replaceable tube configured to guide a radiographic source capsule between a stored position and an exposed position in which at least a portion of the radiographic source capsule is exposed to an exterior of the radiographic shield.

16 Claims, 12 Drawing Sheets

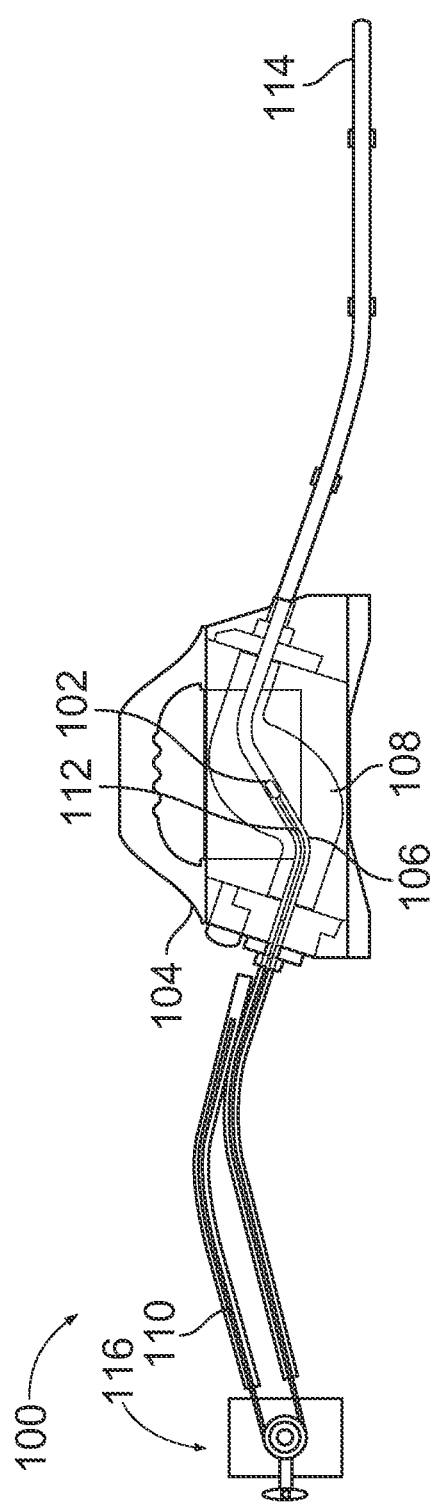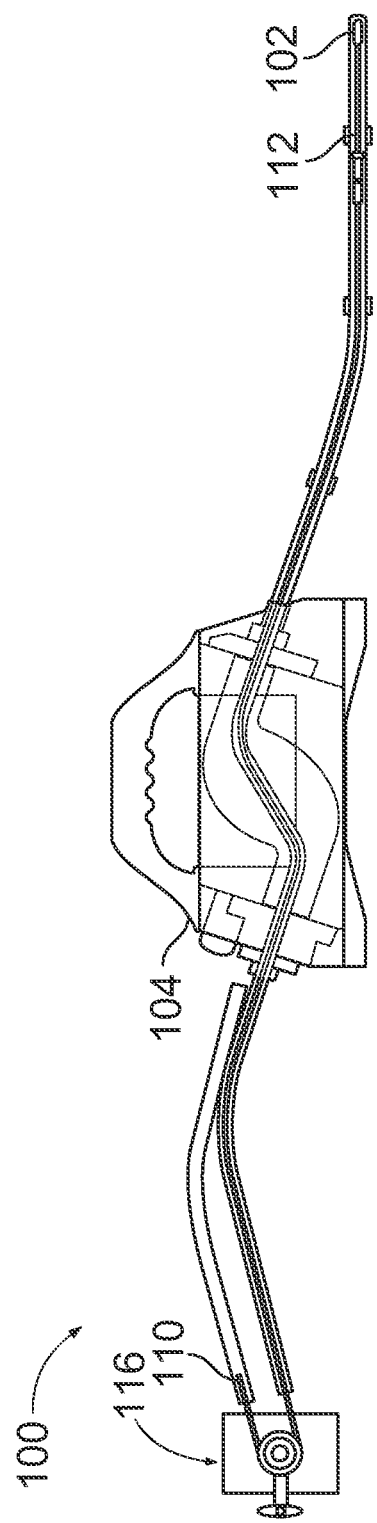
FIG. 1A
FIG. 1B

METHODS AND APPARATUS FOR RADIOGRAPHIC SOURCE EXPOSURE

FIELD OF THE DISCLOSURE

This disclosure relates generally to radiography and, more particularly, to methods and apparatus for radiographic source exposure.

BACKGROUND

Industrial radiography is often used for producing images of objects that are otherwise difficult to inspect, and involves exposing a source of high-energy radiation (e.g., gamma rays) and collecting penetrating and/or reflected rays to form a radiographic image. When not in use, gamma ray sources, such as radioactive isotopes, are stored in shielding devices.

SUMMARY

Methods and apparatus for radiographic source exposure are disclosed, substantially as illustrated by and described in connection with at least one of the figures, as set forth more completely in the claims.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIGS. 1A and 1B illustrate example radiographic system for providing radiation for radiography, in accordance with aspects of this disclosure.

The figures are not necessarily to scale. Wherever appropriate, similar or identical reference numerals are used to refer to similar or identical components.

DETAILED DESCRIPTION

Figure 2:
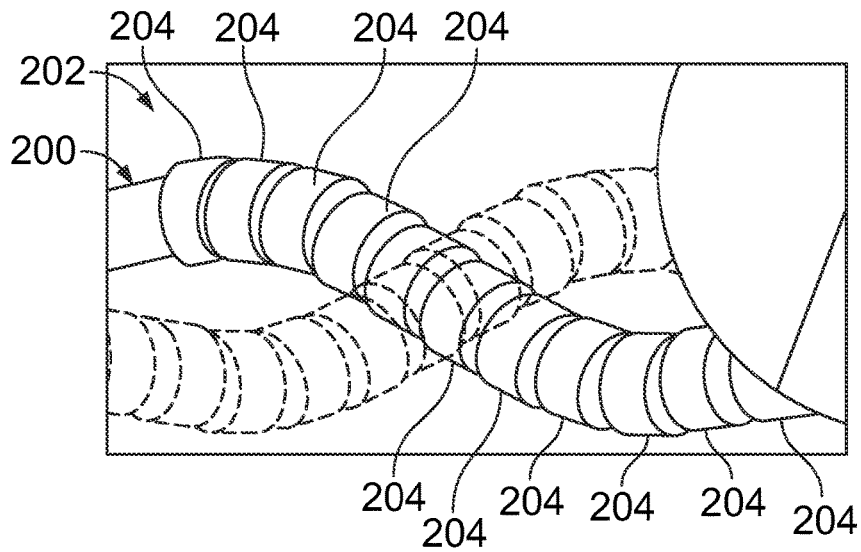
FIG. 2 illustrates an example guide tube, which may be used to implement the guide tube of FIGS. 1A and 1B, and including a tube positioner, having overlapping sections having frictional engagement, which retains the guide tube in a substantially constant position.

For the purpose of promoting an understanding of the principles of the claimed technology and presenting its currently understood, best mode of operation, reference will be now made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would typically occur to one skilled in the art to which the claimed technology relates.

As used herein, the term "radiographic source" refers to a quantity of a radionuclide which provides one or more ionizing electromagnetic radiation emissions (e.g., X-rays, gamma rays, etc.) useful in radiographic applications.

Disclosed example source tubes for radiographic source exposure include: a tube configured to guide a radiographic source capsule from a first end of the tube toward a second end of the tube; a connector to connect the first end of the tube to a radiographic source housing; and a tube positioner coupled along at least a portion of the length of the tube, the tube positioner configured to permit repositioning of the tube in response to physical manipulation of the tube positioner and, when the physical manipulation of the tube positioner is stopped, to retain the tube in a substantially constant position.

In some example source tubes, the tube positioner includes one or more wires coupled along the portion of the length of the tube. In some example source tubes, the tube positioner includes a plurality of overlapping sections, each of the sections configured to have at least a threshold frictional engagement with adjacent sections to retain the tube in the substantially constant position.

Disclosed example guide tubes for radiographic source exposure include: a conduit configured to guide a radiographic source capsule from a first end of the conduit toward a second end of the conduit; a connector to connect the first end of the conduit to a radiographic source housing; and a jacket over the conduit which provides a visual indication in response to lacerations, abrasions, or strain on the jacket.

In some example guide tubes, the jacket has at least a first color and which provides the visual indication as a second color. In some example guide tubes, the jacket is impregnated with dye-containing particles, wherein ones of the particles which are affected by the lacerations, abrasions, or strain on the jacket release dye to create the visual indication at the location of the lacerations, abrasions, or strain.

Other disclosed example guide tubes for radiographic source exposure include: a conduit configured to guide a radiographic source capsule from a first end of the conduit toward a second end of the conduit, the conduit including a mechanochromic material which provides a visual indication in response to mechanical stress; and a connector to connect the first end of the conduit to a radiographic source housing.

In some example guide tubes, the conduit is constructed with the mechanochromic material. In some example guide tubes, the conduit is coated with the mechanochromic material.

Disclosed example radiographic source exposure devices include: a radiographic source capsule having a radionuclide; a radiographic shield; a passageway within the radiographic shield, the passageway having a first end and a second end; and a replaceable tube configured to guide a radiographic source capsule between a stored position and an exposed position in which at least a portion of the radiographic source capsule is exposed to an exterior of the radiographic shield.

In some example radiographic source exposure devices, the replaceable tube is an S-shaped source tube, a U-shaped source tube, a helical source tube, or a straight source tube. In some example radiographic source exposure devices, the radiographic shield includes at least a first portion and a second portion configured to mate with the first portion to form the radiographic shield, and the passageway is formed in at least one of the first portion or the second portion. In some example radiographic source exposure devices, the first portion and the second portion of the radiographic shield include a clamshell arrangement which permits replacement of the replaceable tube in an opened position and provides shielding of the radiographic source capsule in a closed position. In some example radiographic source exposure devices, the first portion and the second portion are detachable. In some example radiographic source exposure devices, the first section of the radiographic shield includes a first portion of the channel, and a second section of the radiographic shield includes a second portion of the channel. In some example radiographic source exposure devices, a shield break line between the first section and the second section of the radiographic shield is offset from a channel break line between the first portion of the channel and the second portion of the channel.

In some example radiographic source exposure devices, the radiographic shield further includes a third section and a fourth section, in which the first section and the second section enclose the channel from a first direction, and the third section and the fourth section are coupled to the first second and the second section in a second direction different than the first direction. In some example radiographic source exposure devices, the first section and the second section have interfacing surfaces that have a non-linear break line between the sections.

In some example radiographic source exposure devices, the interfacing surfaces comprise at least one of a wave shape, an egg crate shape, a wedge shape, a pyramid shape, or a grid shape, in which peaks of the surface of the first section correspond to valleys of the surface of the second section.

In some example radiographic source exposure devices, the radiographic shield does not have any direct unshielded lines or paths from a storage position of the replaceable tube to an exterior of the shield. In some example radiographic source exposure devices, the tube includes a first material adjacent a storage position of the tube, and a second material in a bending portion of the tube. In some example radiographic source exposure devices, the second material has a higher wear resistance than the first material. In some example radiographic source exposure devices, the second material is at least one of stainless steel, tungsten carbide, or ceramic. In some example radiographic source exposure devices, the first material is tungsten or titanium. In some example radiographic source exposure devices, the replaceable tube has a first wall thickness adjacent a storage position of the tube, and a second wall thickness in a bending portion of the tube, wherein the second wall thickness is greater than the first wall thickness.

Other example radiographic source exposure devices include: a housing having a radioactivity shield; a radiographic source configured to be moved between a stored position within the shield and an exposed position at least partially exposed to a location external to the shield; a remote control interface configured to physically connect the radiographic source to a remote control cable of a remote control to control the position of the radiographic source; a source lock configured to mechanically prevent movement of the radiographic source from the stored position while the source lock is in a locked position; and a remote unlocking interface configured to mechanically couple the source lock to a lock release on the remote control to enable the lock release on the remote control to change the source lock to an unlocked position for movement of the radiographic source to the exposed position.

Disclosed example remote controls for a radiographic source include: a drive cable configured to extend into and through a radiographic source housing, to expose a radiographic source to an exterior of the housing, and to retract into and through the radiographic source housing to retract the radiographic source into the radiographic housing; and an unlocking connection configured to couple an unlocking switch on the remote control to a locking device on the radiographic source housing.

In some example remote controls, the unlocking connection includes at least one of an unlocking cable, an electronic signal line, a pneumatic line, hydraulic lines, or a wireless communications connection.

Other example radiographic source exposure devices include: a housing having a radioactivity shield; a radiographic source configured to be moved between a stored position within the shield and an exposed position at least partially exposed to a location external to the shield; a source lock configured to mechanically prevent movement of the radiographic source from the stored position while the source lock is in a locked position; and an unlocking switch positioned on an exterior of the housing, wherein the unlocking switch is at least partially recessed into the housing and the unlocking switch and the recess are dimensioned for activation of the unlocking switch by foot.

Other example radiographic source exposure devices include: a housing having a radioactivity shield; a radiographic source configured to be moved between a stored position within the shield and an exposed position at least partially exposed to a location external to the shield; a source lock configured to mechanically prevent movement of the radiographic source from the stored position while the source lock is in a locked position; and an unlocking switch positioned on an exterior of the housing and configured to receive an externally engaging key to place the source lock into an unlocked position.

In some example radiographic source exposure devices, the unlocking switch is biased to return the source lock to the locked position when the key is removed.

FIGS. 1A and 1B illustrate example radiographic system 100 for providing radiation for radiography. The radiographic system 100 of FIG. 1 includes a radiographic source 102 which is contained within a radiographic source housing 104. The example radiographic source 102 is a mass of radioactive material which emits radiation (e.g., X-rays and/or gamma rays) due to decay of the material.

The radiographic source housing 104 includes an S-shaped source tube 106 within a shield 108. The source tube 106 provides a pathway for the radiographic source 102 to be exposed to an exterior of the shield 108 and retracted to a shielded position within the interior of the shield 108. FIG. 1A illustrates the radiographic source 102 in the shielded position, and FIG. 1B illustrates the radiographic source in an exposed position.

To control the position of the radiographic source 102, the radiographic source housing 104 enables connection of a control cable 110 to the radiographic source 102 for exposure and retraction of the radiographic source 102. The control cable 110 may be physically attached or connected to a pigtail connector 112 that is physically coupled to the radiographic source 102.

When engaged, the control cable 110 is controlled to extend into and through the source tube 106 to push the radiographic source 102 to an exposed position external to the radiographic source housing 104. Conversely, the control cable 110 is retracted to pull the radiographic source 102 from the exposed position back into the source tube 106 to the shielded position, at which time the control cable 110 may be detached from the radiographic source 102.

In the system 100 of FIG. 1, the exposed position of the radiographic source 102 may be controlled by a guide tube 114, through which the radiographic source 102 travels as the source 102 is pushed by the control cable 110. The control cable 110 has sufficient column strength to push the radiographic source 102 through the source tube 106 and through the guide tube 114.

The control cable 110 is controlled by a remote control 116. The remote control 116 physically engages the control cable 110 to advance or retract the control cable 110 relative to the remote control 116.

FIG. 2 illustrates an example guide tube 200, which may be used to implement the guide tube 114 of FIGS. 1A and 1B. The example guide tube 200 includes a tube positioner 202 having overlapping sections 204. The sections 204 extend along the length of at least a portion of the guide tube 200.

The sections 204 of the tube positioner 202 have frictional engagement with adjacent sections 204. The frictional engagement provides sufficient force to retain the tube positioner 202 and guide tube 200 stationary in a configured position, but also permits manual repositioning of the guide tube 200 and tube positioner 202 by an operator.

In some examples, the sections 204 are separate components which are assembled onto the guide tube 200, such that the overlapping sections have sufficiently high friction to resist movement under the weight of the guide tube 200 and an exposed radiographic source within the guide tube 200.

In some other examples, a tape of material is wrapped around the guide tube 200 in an overlapping manner to form the overlapping sections 204. The separate sections or single, overlapping tape may have any desired cross-sectional shape to improve friction and/or interlocking of the sections 204.

Figure 3:
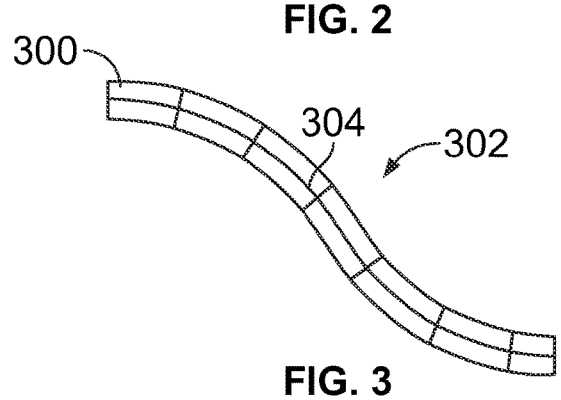
FIG. 3 illustrates another example guide tube, which may be used to implement the guide tube of FIGS. 1A and 1B, and including a tube positioner having one or more wires extending along a length of the guide tube to retain the guide tube in a substantially constant position.

FIG. 3 illustrates another example guide tube 300, which may be used to implement the guide tube 114 of FIGS. 1A and 1B, and including a tube positioner 302 having one or more wires 304 extending along a length of the guide tube 300. The wires 304 may be secured to an exterior and/or interior of the guide tube 300 to regular or irregular intervals. The wires 304 may be arranged and attached to the guide tube 300 such that bending of the tube positioner 302 and guide tube 300 to the desired shape does not crush the guide tube 300 or otherwise impede extension and/or retraction of the radiographic source. For example, two wires attached an arcuate angle between 0 and 180 degrees, or more preferably between 60 and 120 degrees, may reduce or avoid impeding of the radiographic source.

The wires 304 are formed from steel, aluminum, and/or any other material and corresponding diameter to be both manipulable by an operator into a desired shape of the guide tube 300, and to retain the configured shape of the guide tube 300 in a stationary position when released by the operator.

Figure 4A:
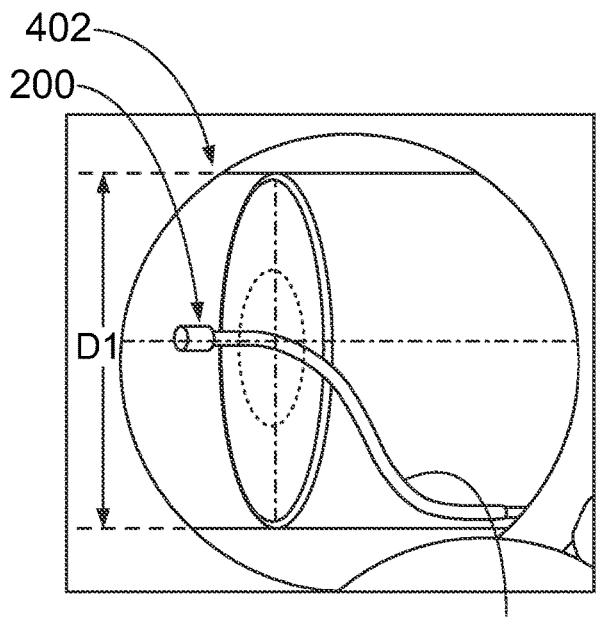
FIGS. 4A and 4B illustrate the example tube positioner of FIG. 2 retaining the guide tube in different positions for radiographic inspection of objects having different dimensions.
Figure 4B:
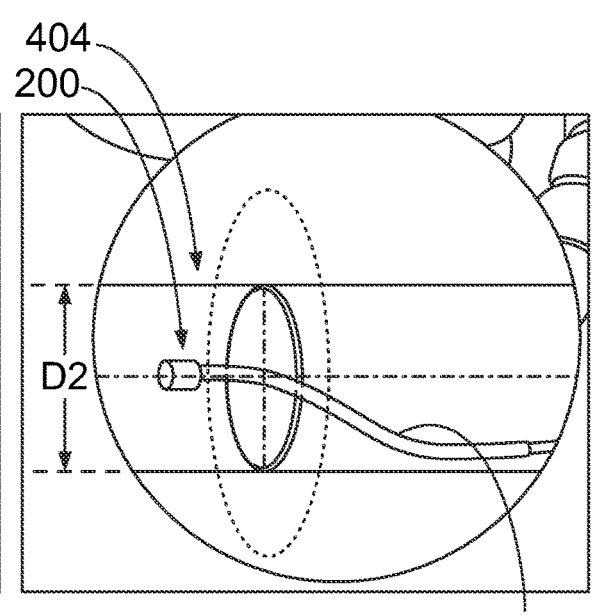

FIGS. 4A and 4B illustrate the example tube positioner 202 of FIG. 2 retaining the guide tube 200 in different positions for radiographic inspection of objects 402, 404 (e.g., pipes under inspection) having different dimensions. The example object 402 is a first pipe having a first diameter D1, and the example object 404 is a second pipe having a second diameter D2.

In each example object 402, 404, an inspection procedure may require positioning of the exposed radiographic source near a center of the cross section of the object 402, 404. The same radiographic source and guide tube 200 may be used for both inspections by physically configuring the guide tube 200 and tube positioner 202 to position the guide tube 200 (e.g., an end of the guide tube 200) substantially at the center of the object 402, 404. For example, the guide tube 200 and tube positioner 202 may require a larger bend to position the guide tube 200 at the center of the first object 402 having a larger diameter D1, and a smaller bend to position the guide tube 200 at the center of the second object 404 having a smaller diameter D2. In each inspection, the tube positioner 202 may rest on a bottom of the object 402, 404 to support the guide tube 200 at the desired position.

Compared with conventional positioning devices, the example guide tubes 200, 300 and tube positioners 202, 302 may improve the speed at which the inspection is conducted.

Figure 5A:
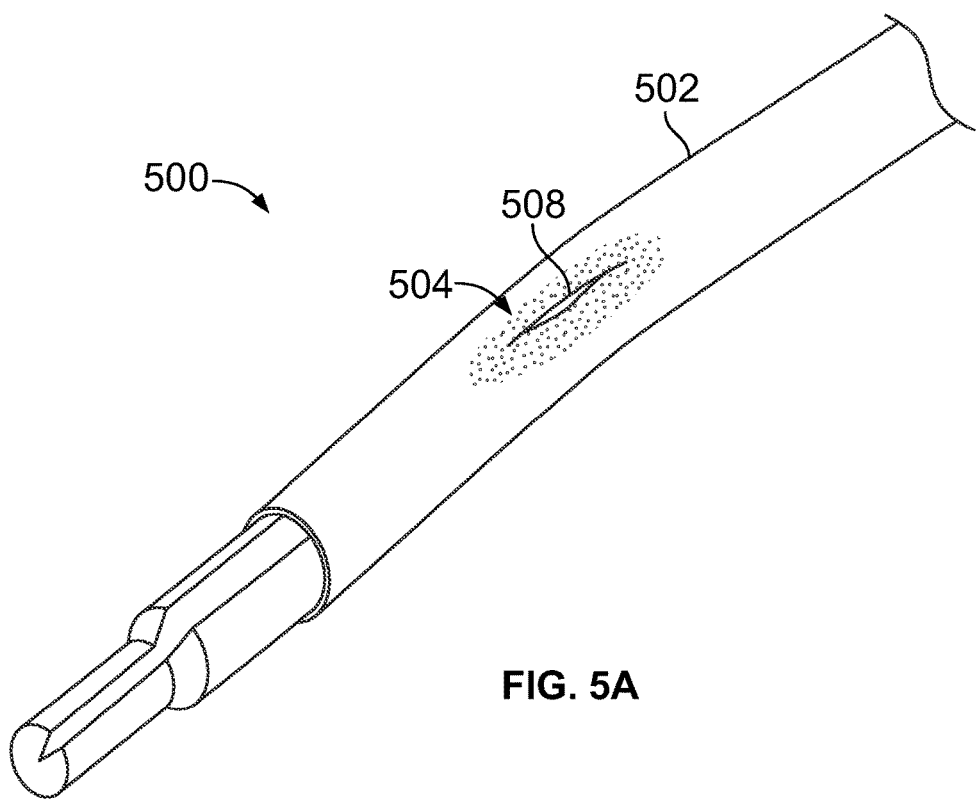
FIGS. 5A and 5B illustrate example guide tubes having jackets which provide visual indications in response to lacerations, abrasions, and/or strain on the jackets.
Figure 5B:
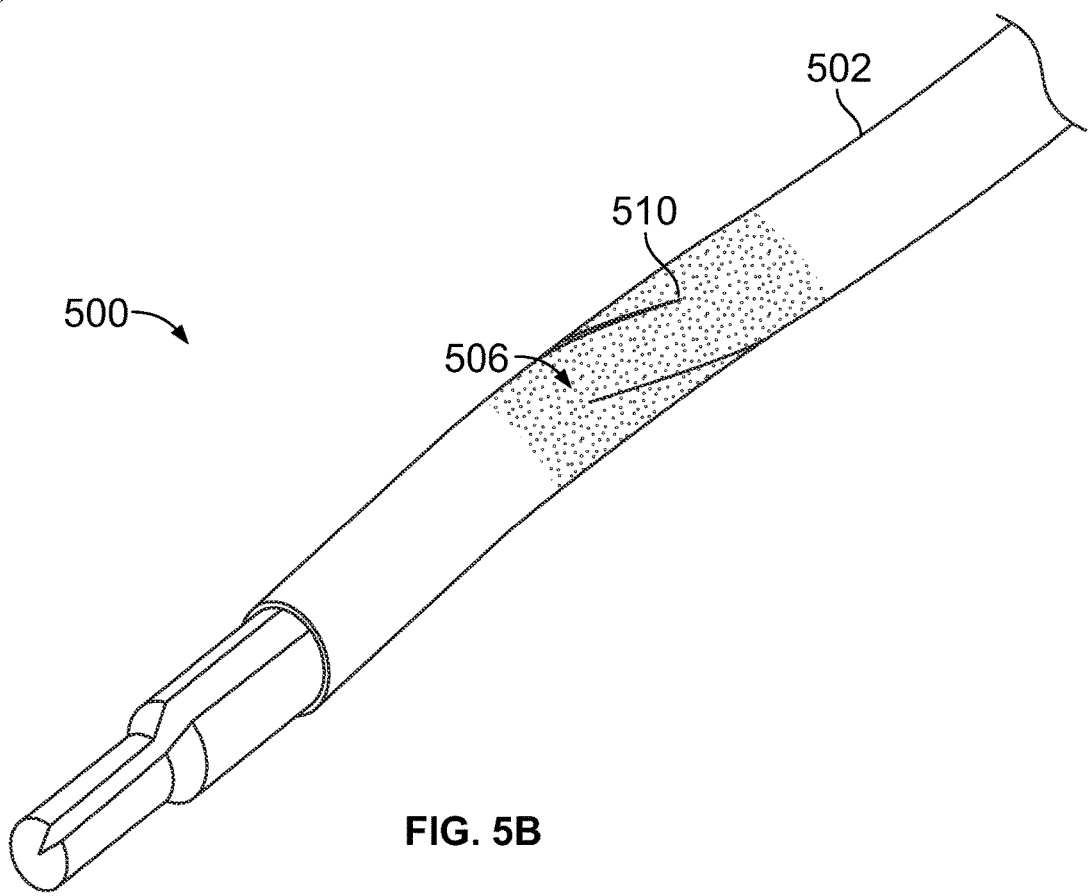

FIGS. 5A and 5B illustrate an example guide tube 500 having a jacket 502 which provide visual indications 504, 506 in response to lacerations, abrasions, strain, and/or other damage to the jacket 502. The jacket 502 may be a sole layer or protective outer layer of the guide tube 500.

The example jacket 502 responds to lacerations (e.g., cut 508 illustrated in FIG. 5A), abrasions, and/or strain (e.g., twisting strain 510 illustrated in FIG. 5B) by introducing a different (e.g., contrasting) color onto the jacket 502 at and/or around the location of the damage. The visual indications 504, 506 increase the likelihood that damage will be identified during inspection and/or use of the guide tube 500.

To provide the visual indication, the example jacket 502 may be impregnated, coated, and/or otherwise provided with microbeads, or other container type or structure, filled with dye, reactive chemistry, and/or any other material which results in a visually identifiable change in the appearance of the jacket 502. For example, when the jacket 502 is cut (FIG. 5A) or incurs a sufficient twisting strain 510 (FIG. 5B), dye-containing microbeads within and/or on the jacket 502 are ruptured. The dye disperses to and/or over the outside of the jacket 502, where the dye may be more easily observed than the cut 508 or strain 510 itself.

The microbeads or other structure may be formulated and/or structured to rupture and disperse their contents at a similar range of twisting strain as would render the guide tube 500 unsuitable for use.

Additionally or alternatively, a conduit portion of the guide tube 500 provides visual indications of excessive mechanical stress. For example, excessive stress on the guide tube 500 can cause kinking, denting, or other obstructions to extension or retraction of the radiographic source through the guide tube 500. To visually indicate excessive stress, the conduit portion of the guide tube 500 may be constructed and/or coated with mechanochromic materials that cause a visual (e.g., color) change in response to mechanical stresses. The mechanochromic material(s) used in the conduit may be based on the stress limit(s) allowed on the guide tube 500.

Figure 6A:
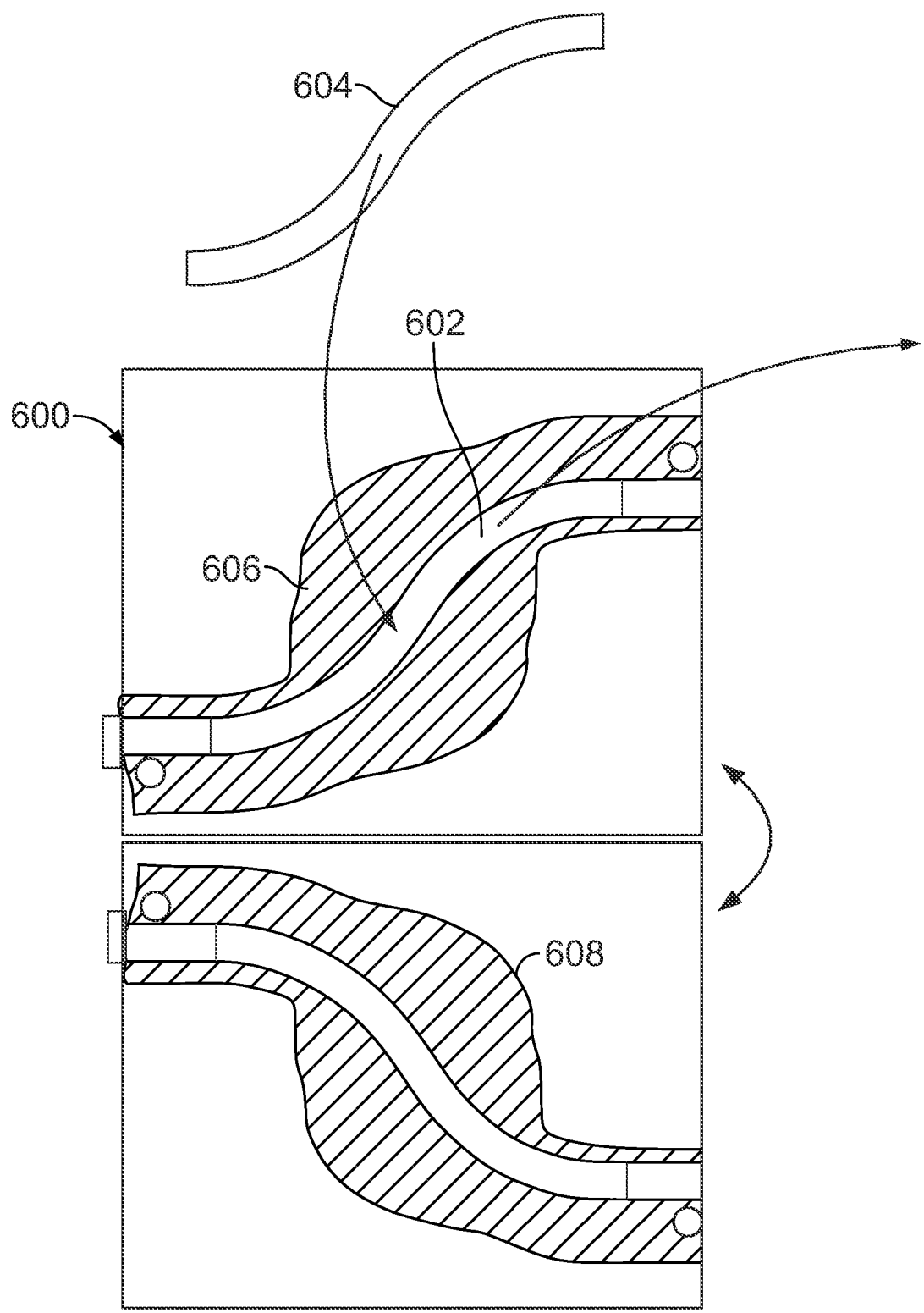
FIG. 6A illustrates an example radiographic shield having a replaceable source tube for the radiographic source within the radiographic source exposure device.

FIG. 6A illustrates an example radiographic shield 600 having a replaceable source tube 602 for a radiographic source within a radiographic source exposure device. Conventional source tubes are subject to wear due to abrasion by a control cable and/or introduction of foreign particles or contaminants into the source tube 602 by the control cable. Conventional source tubes are cast into a shielding material, such as depleted uranium. When a cast source tube is worn through, scrapping of the radiographic exposure device is generally required.

The example radiographic shield 600 is constructed from two or more components, and the source tube 602 of FIG. 6A is removable from the shield 600 and replaceable with a different source tube. The example source tube 602 is S-shaped and constructed from titanium. As a result, when threshold wear is detected in the source tube 602 (or for any other reason), the radiographic shield 600 may be disassembled to replace the source tube 602 with a new or otherwise useable source tube 604, and then reassembled for continued use.

As used herein, the term "removable tube" refers to a tube and shield construction having the capability of removal of the tube from the shield without damage to the shield. For example, a removable tube may be mechanically secured using fasteners, welding, adhesive, and/or any other mechanical attachment techniques, provided that the mechanical attachment techniques are reversible to remove the tube (without damage to the shield) and/or reproducible for a replacement tube.

The example radiographic shield 600 includes a first portion 606 and a second portion 608, but the shield 600 may include more than two separate portions. The example first and second portions 606, 608 of FIG. 6A are connected in a clamshell configuration, but may be separable.

A bore or channel for the source tube 602 may be present in one or both of the portions 606, 608. For example, the source tube 602 may be seated completely into the first portion 606, and the second portion 608 has a flat surface to retain the source tube 602 in the first portion 606. Furthermore, while the example radiographic shield 600 has a source tube, other examples may have differently shaped tubes, radiographic source paths, and/or radiographic source storage positions.

In other examples, the shield 600 is a single-piece (e.g., cast) shield from which the source tube 602 can be extracted and replaced. Additionally or alternatively, the source tube 602 may have different shapes which can be replaceable in single-piece and/or multi-piece shields, such as S-shaped source tube, a U-shaped source tube, a helical source tube, or a straight source tube, and/or any other shape capable of being removed and inserted into a shield.

Figure 6B:
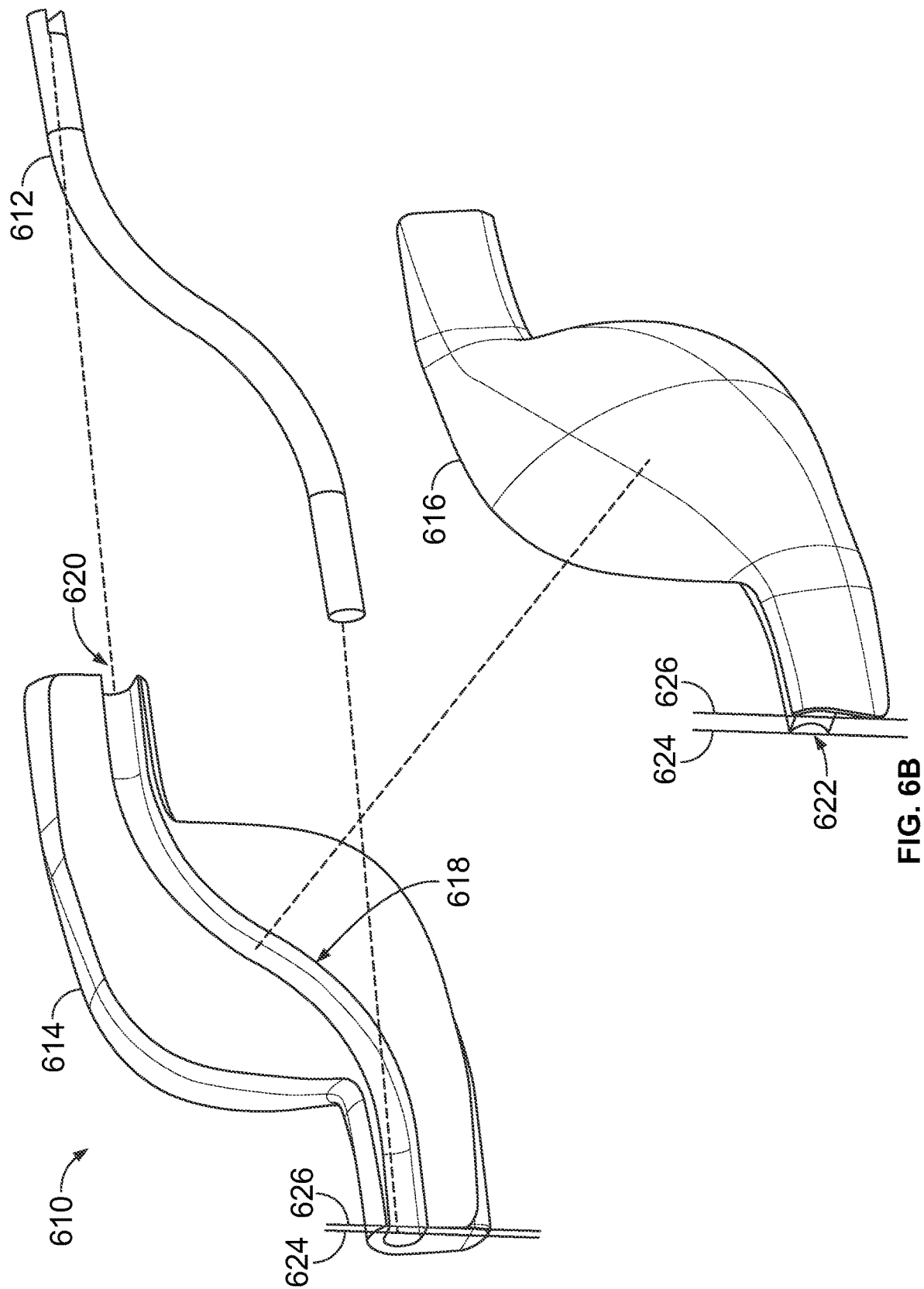
FIG. 6B is an exploded view of another example radiographic shield having a removable and/or replaceable source tube for a radiographic source within a radiographic source exposure device.

FIG. 6B is an exploded view of another example radiographic shield 610 having a removable and/or replaceable source tube 612 for a radiographic source within a radiographic source exposure device. The example radiographic shield 610 includes a first section 614 and a second section 616. The first and second sections 614, 616 are constructed to eliminate any direct unshielded lines or paths from the storage position of the source (e.g., in a center of the source tube 612).

Figure 6C:
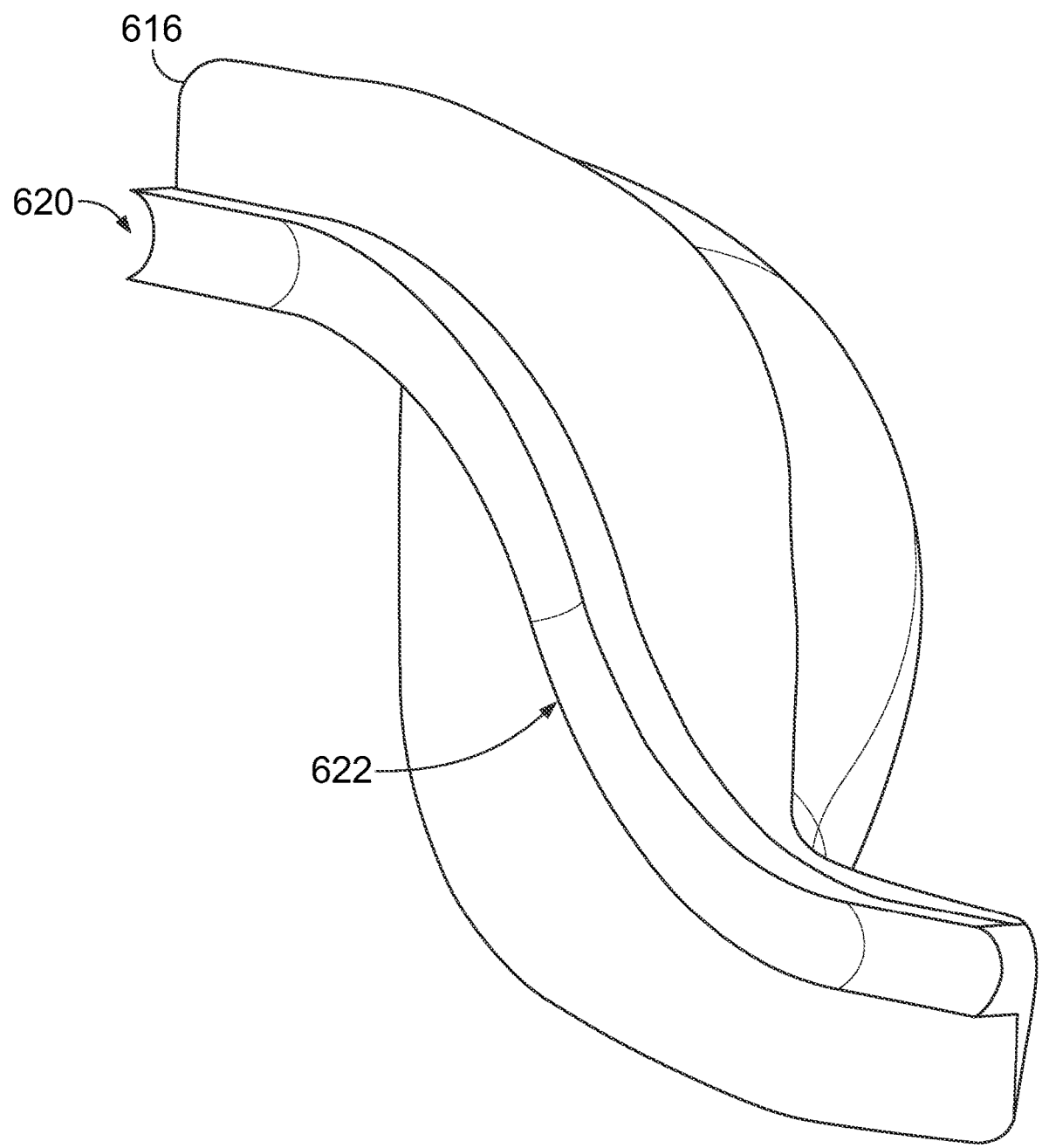
FIG. 6C is another view of the example second section of the shield of FIG. 6B.

The first example section 614 has a first portion 618 of a channel 620, into which the source tube 612 is seated. The second example section 616 has a second portion 622 of the channel 620. FIG. 6C is another view of the example second section 616 of the shield 610 of FIG. 6B. When assembled, the source tube 612 is seated within the channel 620, and the sections 614, 616 of the shield 610 are coupled together to secure the source tube 612 within the channel 620. The first and second portions 618, 622 of the channel 620 have a channel break line 624 that is offset from a shield break line 626 of the remainder of the sections 614, 616. As a result, a source positioned in the center of the source tube 612, and does not have any direct unshielded lines or paths from the storage position of the source tube 612 to the exterior of the shield 610.

In some examples, the sections 614, 616 may be disassembled for removal and/or replacement of the source tube 612, and reassembled to secure a replacement source tube 612 into the channel 620.

Figure 6D:
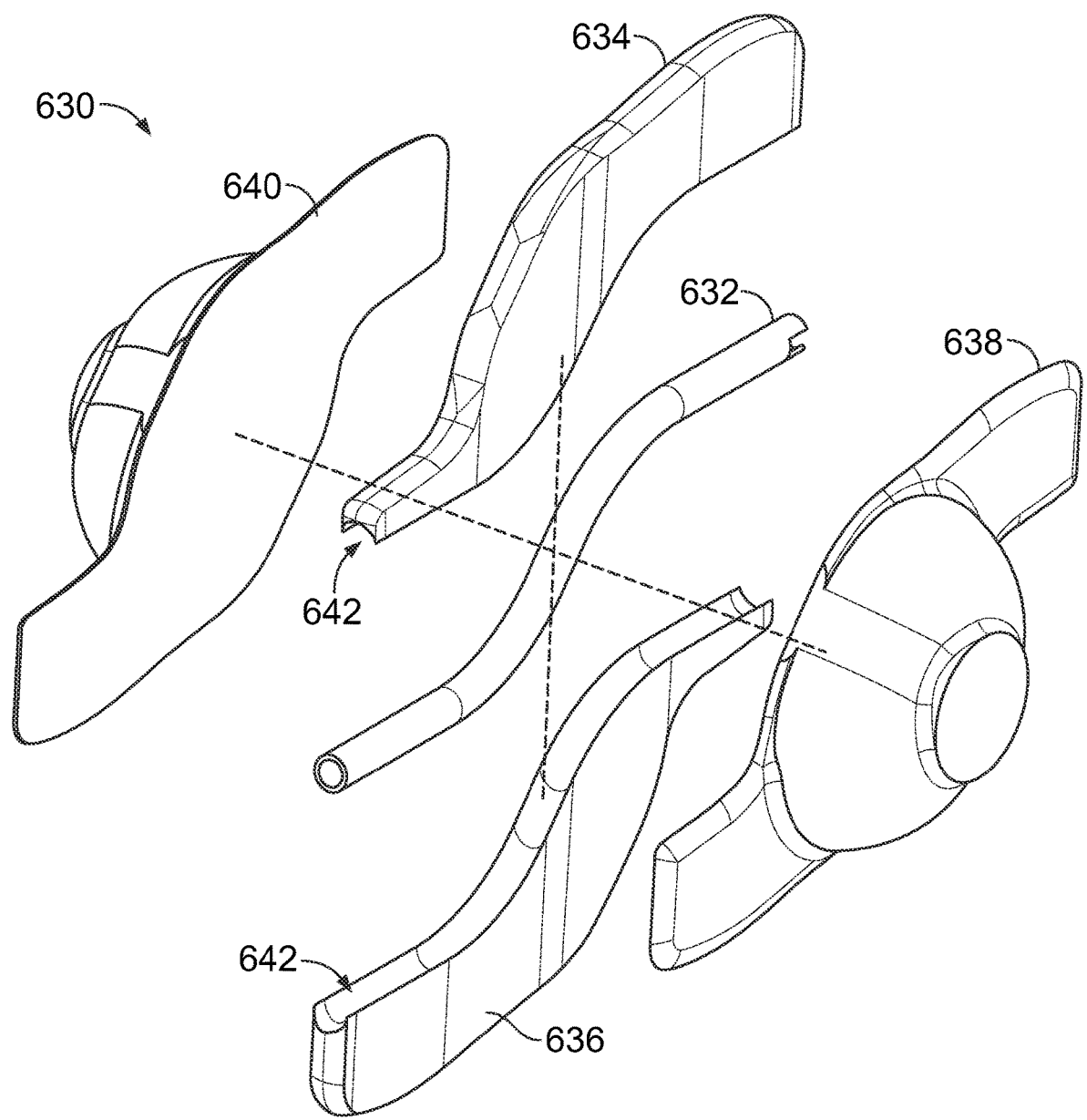
FIG. 6D is an exploded view of another example radiographic shield having a removable and/or replaceable source tube for a radiographic source within a radiographic source exposure device.

FIG. 6D is an exploded view of another example radiographic shield 630 having a removable and/or replaceable source tube 632 for a radiographic source within a radiographic source exposure device. The example shield 630 of FIG. 6D includes four sections 634, 636, 638, 640.

The sections 634, 636 form a channel 642 into which the source tube 632 is seated and secured. The sections 638, 640 shield the channel 642, the source tube 632, and at least a portion of each of the sections 634, 636. The sections 634-640 of the shield 630 are constructed to eliminate any direct unshielded lines or paths from the storage position of the source (e.g., in a center of the source tube 632). Additionally, the sections 634-640 are dimensioned to have a concentration of shielding around the storage position of the source (e.g., the center of the source tube 632.

In some examples, the sections 634-640 be disassembled for removal and/or replacement of the source tube 632, and reassembled to secure a replacement source tube 632 into the channel 642.

Figure 6E:
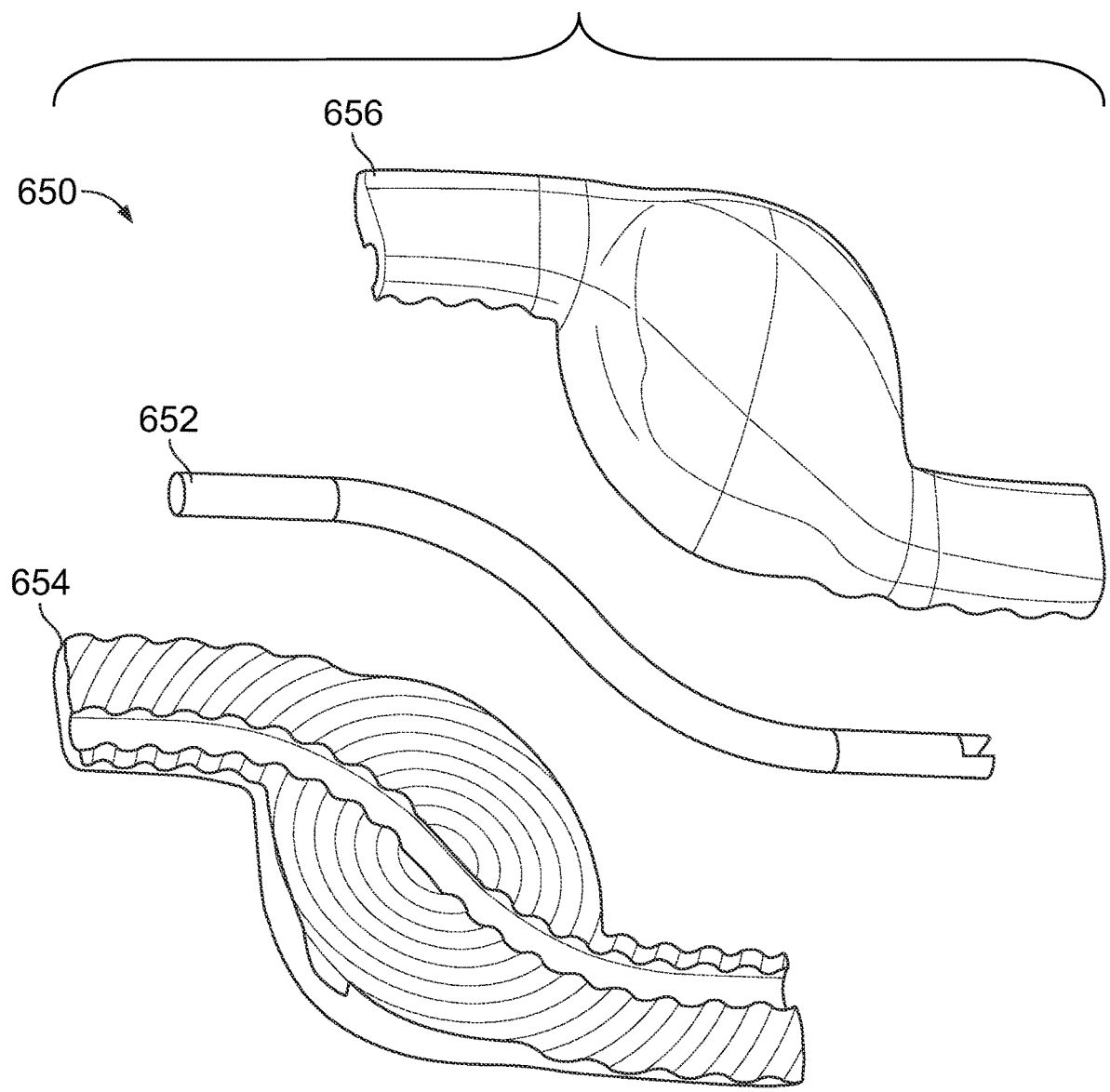
FIG. 6E is an exploded view of another example radiographic shield having a removable and/or replaceable source tube for a radiographic source within a radiographic source exposure device.

FIG. 6E is an exploded view of another example radiographic shield 650 having a removable and/or replaceable source tube 652 for a radiographic source within a radiographic source exposure device. The example shield 650 of FIG. 6E includes two sections 654, 656 which define a channel 658 into which the source tube 652 is seated.

Instead of having different break lines for the channel 658 and the sections 654, 656 as in the example of FIG. 6B, the example sections 654, 656 have interfacing surfaces that have a non-linear break line between the sections 654, 656. In the example of FIG. 6E, the sections 654, 656 have coordinating surfaces, such as the illustrated wave-shaped surfaces in which the peaks and valleys of the section 654 correspond to the valleys and peaks, respectively, of the section 656. As a result, the break line between the sections 654, 656 precludes a direct unshielded line or path to the exterior of the shield 650. Other surface contours may be used, such as an egg crate shape, a wedge shape, a pyramid shape, and/or a grid shape.

The example source tubes 612, 632, 652 of FIGS. 6A-6E may be a uniform shielding material, such as tungsten or titanium. In other examples, the source tubes 612, 632, 652 may be constructed using multiple materials, such as a heavier shielding material (e.g., tungsten, titanium) in the regions closer to the storage position of the source and/or in straight sections of the source tubes 612, 632, 652, and a harder, more wear-resistant material near the bends in the storage tubes 612, 632, 652. Example wear-resistant materials that may be positioned at the bends of the storage tubes 612, 632, 652 include stainless steel (e.g., 316 alloy or other alloys), tungsten carbide, and/or a suitable ceramic material.

Such a composite source tube provides a higher useful life of the source tube, and reduces the frequency of disassembly for replacement of the source tube. In examples in which the source tube is not replaceable (e.g., the source tube is cast into the shield), the composite source tube having a harder material at the bends may increase the service life of the radiographic source exposure device.

Figure 6F:
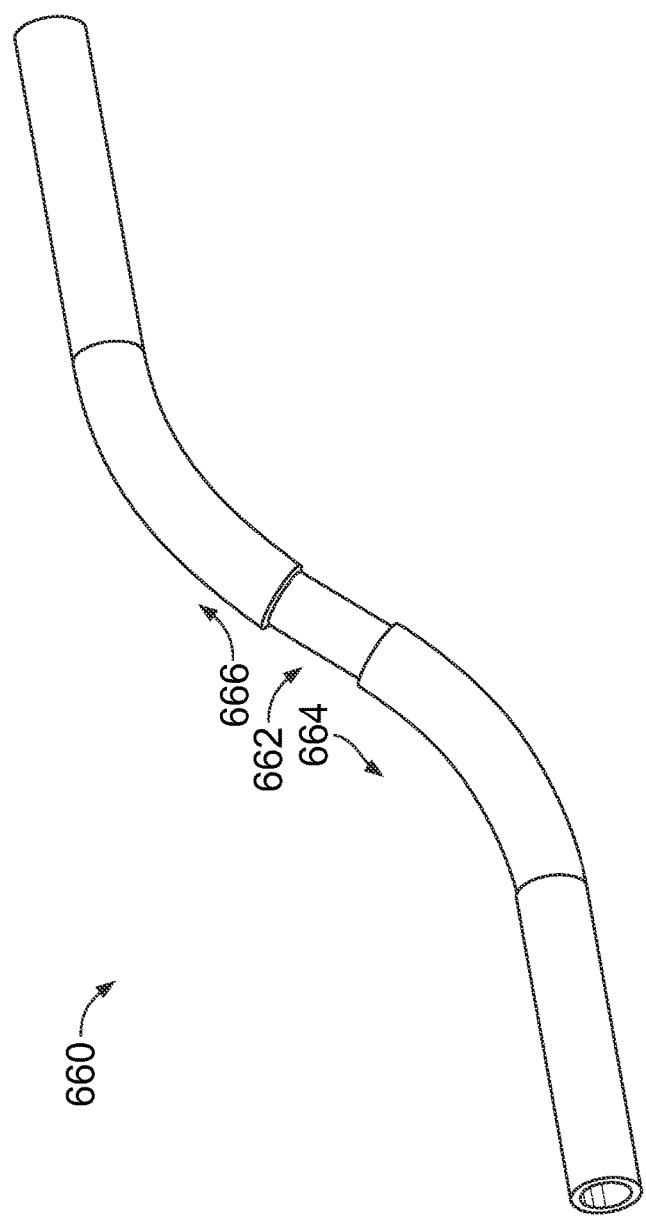
FIG. 6F illustrates another example source tube that may be used to implement any of the example source tubes of FIGS. 6A-6E, in which the source tube has a different wall thickness at different portions of the source tube.

FIG. 6F illustrates another example source tube 660 that may be used to implement any of the example source tubes of FIGS. 6A-6E, in which the source tube 660 has a different wall thickness at different portions of the source tube 660. As illustrated in FIG. 6F, a central portion 662 of the source tube 660 has a thinner wall relative to other portions 664, 666 of the source tube 660. The thinner wall and re outer diameter at the storage position of the source (e.g., at the central portion 662) allows for the dense shield material to be positioned closer to the gamma source. The closer positioning may lower the surface dose and/or allow for the outside of the shield to be reduced by a same amount, thereby resulting in a weight reduction of the radiographic source exposure device.

Figure 7:
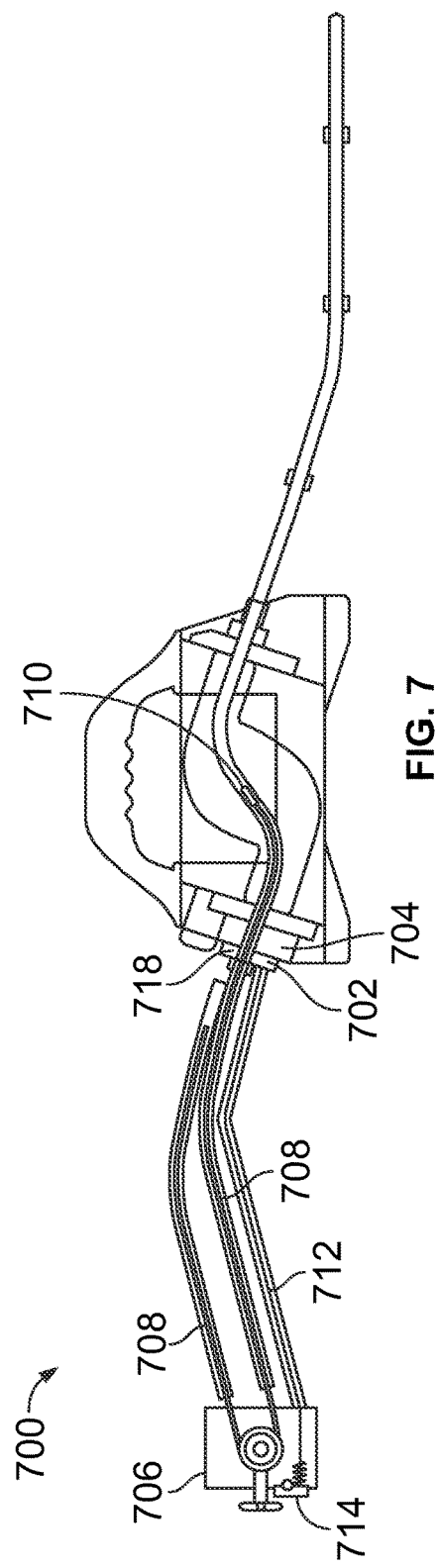
FIG. 7 illustrates an example radiographic source exposure device having a remote unlocking interface for unlocking a locking device from a remote control.

FIG. 7 illustrates an example radiographic source exposure device 700 having a remote unlocking interface 702 for unlocking a locking device 704 from a remote control 706. The remote control 706 allows an operator to advance or retract a control cable 708, which controls the position of a radiographic source 710 when attached via a remote control interface 718.

The locking device 704 prevents exposure of the radiographic source 710 until the locking device 704 is placed in an unlocked position via an unlocking key and/or via an unlocking switch. When placed in an unlocked position, the control cable 708 is released to permit movement of the radiographic source 710 via the control cable 708. In some examples, when the radiographic source 710 returns to a stored position within the exposure device 700 from an exposed position (or a position other than the stored position), the locking device 704 automatically returns to the locked position to prevent unintentional additional exposure.

The example remote control 706 further includes an unlocking cable 712, which couples an unlocking switch 714 on the remote control 706 to the unlocking interface 702 on the locking device 704. The unlocking interface 702 may be combined with, adjacent to, or separate from the remote control interface 718 which connects the control cable 708 to the radiographic source 710. When the remote control 706 is connected to the unlocking interface 716, the unlocking cable 712 connects the unlocking switch 714 to the locking device 704. When the unlocking switch 714 is actuated, the unlocking switch 714 unlocks the locking device 704 to enable the remote control 706 to control the position of the radiographic source 710. The unlocking switch 714 similarly biased to pull the unlocking cable 712 to the locked position in conjunction with the bias of the locking device 704.

Figure 8:
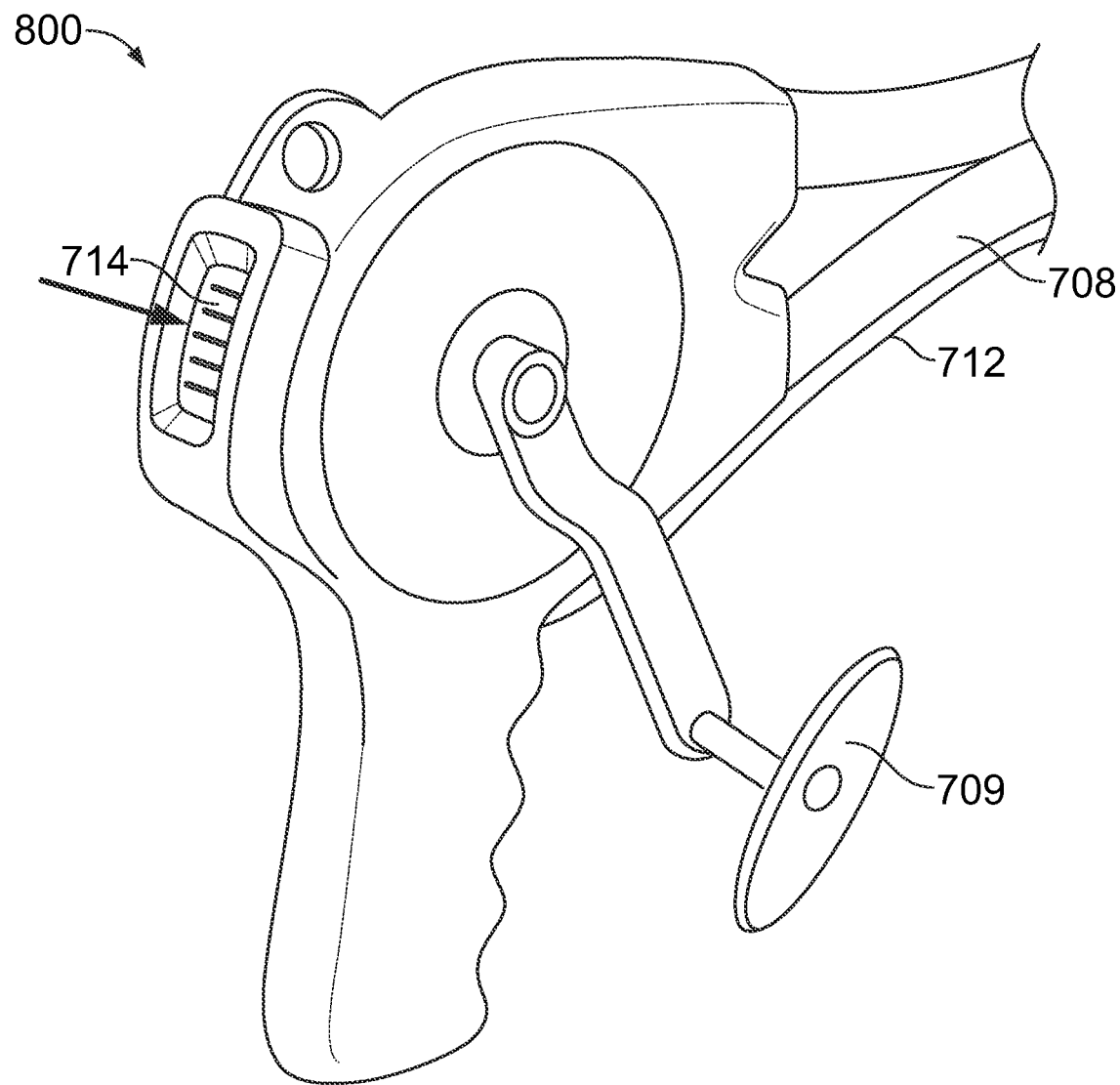
FIG. 8 illustrates an example remote control having an unlocking cable configured to couple an unlocking switch on the remote control to a locking device on the radiographic source housing.

FIG. 8 illustrates an example remote control 800 that may implement the remote control 706 of FIG. 7. The remote control 800 of FIG. 8 includes the unlocking cable 712 configured to couple the unlocking switch 714 on the remote control 800 to the locking device 704 on the radiographic source housing.

In other examples, the remote control 800 may be connected to the locking device 704 via an electronic control (e.g., signal lines between the remote control 800 and the locking device 704), via a pneumatic line, via hydraulic lines, via a wireless communications connection (e.g., wireless communication modules at both the remote control 800 and the locking device 704), and/or via any other connection method.

Figure 9A:
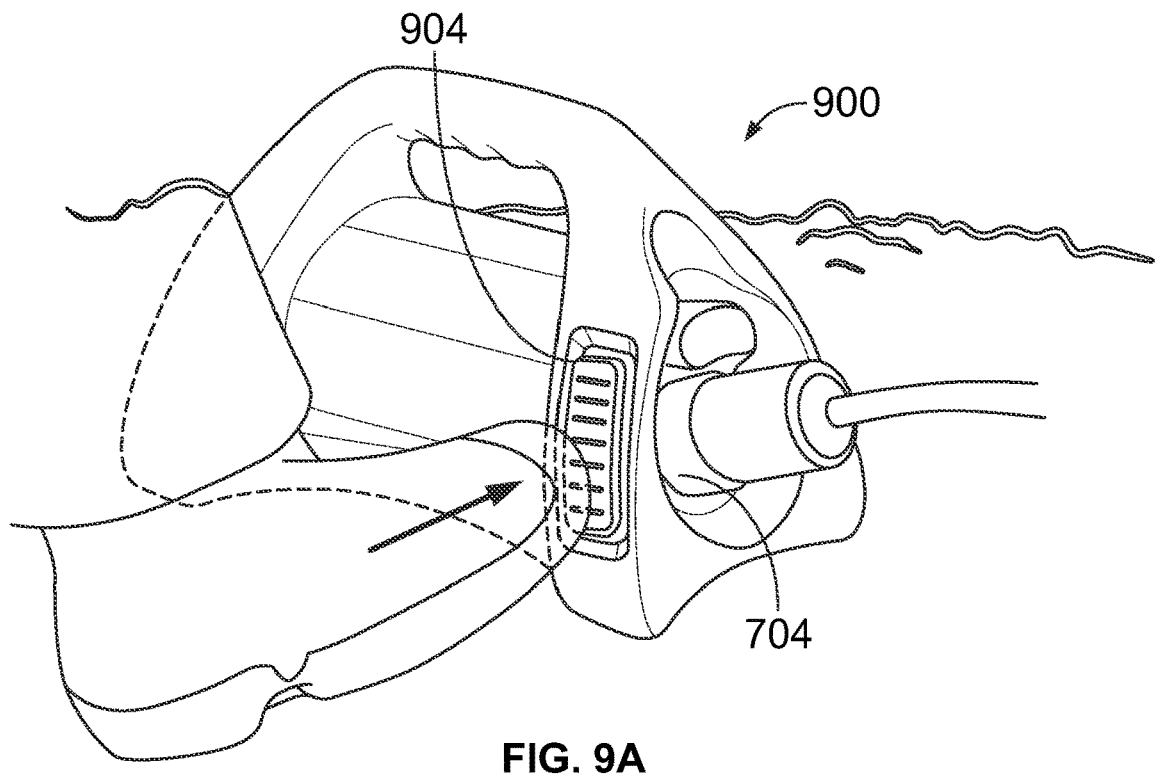
FIGS. 9A and 9B illustrate example radiographic exposure devices having foot-operated unlocking switches for unlocking the radiographic sources.
Figure 9B:
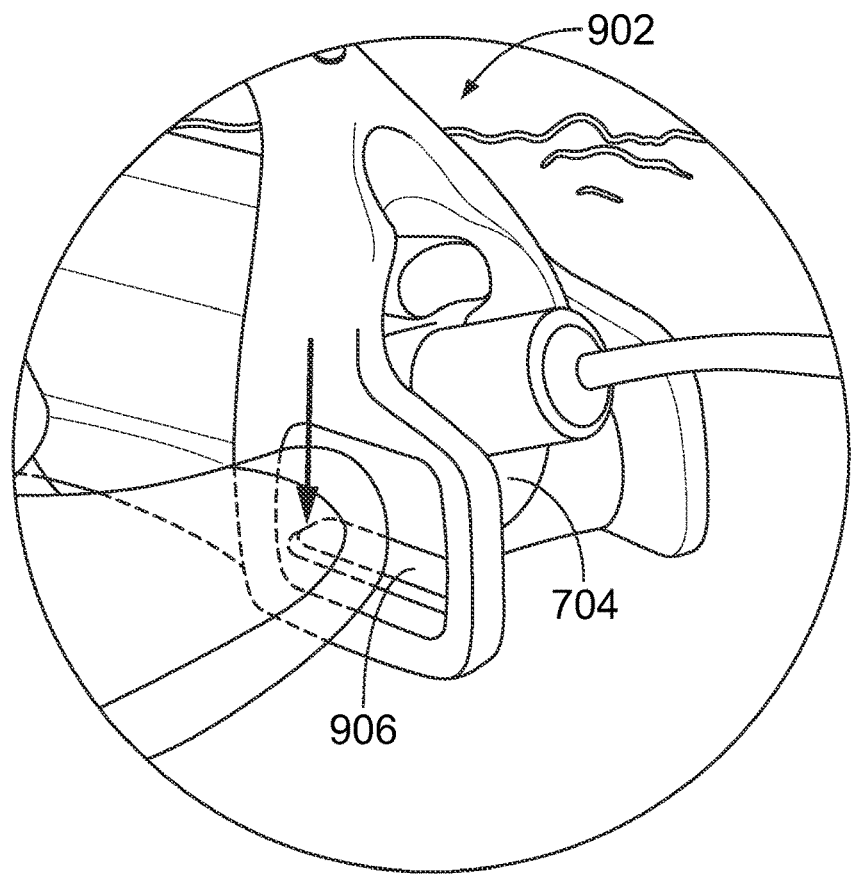

FIGS. 9A and 9B illustrate example radiographic exposure devices 900, 902 having foot-operated unlocking switches 904, 906 for unlocking the radiographic sources. The example radiographic exposure device 900 of FIG. 9A includes a foot-operated switch 904, which can be actuated by pushing the switch 904 inward toward the housing. The switch 904 is connected to the locking device (e g, similar to the locking device 704 of FIG. 7) to unlock a radiographic source. The example radiographic exposure device 902 of FIG. 9B includes a foot-operated switch 906, which can be actuated by pushing the switch 906 downward.

Because the switches 904, 906 are positioned on the housing, the switches 904, 906 may remain in an actuated position and/or hold the locking device 704 in the unlocked position while the operator moves away from the radiographic exposure devices 900, 902, and/or until the radiographic source is moved and returned to an initial stored position within the shielding device. In some examples, when the radiographic source 710 returns to a stored position within the exposure device 700 from an exposed position (or a position other than the stored position), the locking device 704 automatically returns to the locked position to prevent unintentional additional exposure and/or the switches 904, 906 return to a locked or non-actuated position.

Figure 10:
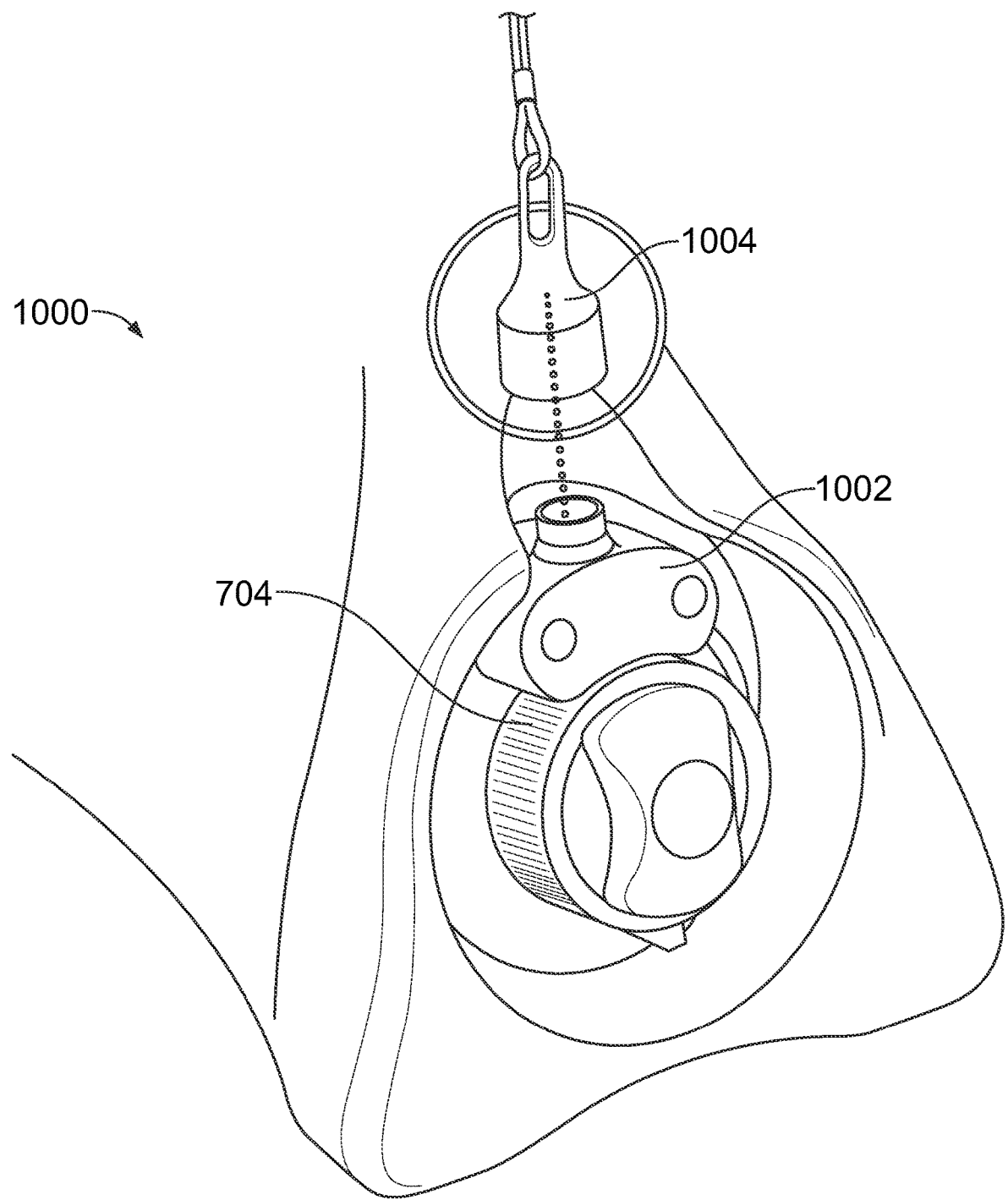
FIG. 10 illustrates another example radiographic exposure device having a key-operated unlocking switch for unlocking the radiographic source.

FIG. 10 illustrates another example radiographic exposure device 1000 having a key-operated unlocking switch 1002 for unlocking the radiographic source. In contrast with conventional key and tumbler locks, the example key-operated unlocking switch 1002 may use a generic, presence-based key 1004 which unlocks the locking device 704 while present. For example, the key 1004 may physically snap into place to actuate the unlocking switch 1002 into an unlocked position. In some other examples, the key 1004 may be magnetic to magnetically actuate the unlocking switch 1002. While the key 1004 is present and actuating the unlocking switch 1002, the unlocking switch 1002 maintains the locking device 704 in an unlocked position. When the key 1004 is removed, the locking device 704 is biased into the locking position, but allows a return of the radiographic source to the storage position from an exposed position, at which time the locking device 704 locks the radiographic source against further exposure until the unlocking switch 1002 is again activated with the key. In contrast with the conventional locks, the example key 1004 is an external-engagement key that does not involve penetration into the unlocking switch 1002 that can result in introduction of particulate and eventual damage to the unlocking switch 1002.

While the example of FIG. 10 is illustrated without the remote control connected, in some examples the locking device 704 requires both actuation of an unlocking switch and the installation of the remote control device at a remote control interface.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A radiographic source exposure device, comprising:
   a radiographic source capsule having a radionuclide;
   a radiographic shield;
   a channel within the radiographic shield, the channel having a first end and a second end; and
   a replaceable tube configured to guide a radiographic source capsule between a stored position and an exposed position in which at least a portion of the radiographic source capsule is exposed to an exterior of the radiographic shield.

2. The radiographic source exposure device as defined in claim 1, wherein the replaceable tube is an S-shaped source tube, a U-shaped source tube, a helical source tube, or a straight source tube.

3. The radiographic source exposure device as defined in claim 1, wherein the radiographic shield comprises at least a first section and a second section configured to mate with the first section to form the radiographic shield, and the channel is formed in at least one of the first section or the second section.

4. The radiographic source exposure device as defined in claim 3, wherein the first section and the second section of the radiographic shield comprise a clamshell arrangement which permits replacement of the replaceable tube in an opened position and provides shielding of the radiographic source capsule in a closed position.

5. The radiographic source exposure device as defined in claim 3, wherein the first section and the second section are detachable.

6. The radiographic source exposure device as defined in claim 3, wherein the first section of the radiographic shield comprises a first portion of the channel, and the second section of the radiographic shield comprises a second portion of the channel.

7. The radiographic source exposure device as defined in claim 6, wherein a shield break line between the first section and the second section of the radiographic shield is offset from a channel break line between the first portion of the channel and the second portion of the channel.

8. The radiographic source exposure device as defined in claim 3, wherein the radiographic shield further comprises a third section and a fourth section, wherein the first section and the second section enclose the channel from a first direction, and the third section and the fourth section are coupled to the first second and the second section in a second direction different than the first direction.

9. The radiographic source exposure device as defined in claim 3, wherein the first section and the second section have interfacing surfaces that have a non-linear break line between the sections.

10. The radiographic source exposure device as defined in claim 9, wherein the interfacing surfaces comprise at least one of a wave shape, an egg crate shape, a wedge shape, a pyramid shape, or a grid shape, in which peaks of the surface of the first section correspond to valleys of the surface of the second section.

11. The radiographic source exposure device as defined in claim 1, wherein the radiographic shield does not have any direct unshielded lines or paths from a storage position of the replaceable tube to an exterior of the shield.

12. The radiographic source exposure device as defined in claim 1, wherein the tube comprises a first material adjacent a storage position of the tube, and a second material in a bending portion of the tube.

13. The radiographic source exposure device as defined in claim 12, wherein the second material has a higher wear resistance than the first material.

14. The radiographic source exposure device as defined in claim 12, wherein the second material comprises at least one of stainless steel, tungsten carbide, or ceramic.

15. The radiographic source exposure device as defined in claim 12, wherein the first material comprises tungsten or titanium.

16. The radiographic source exposure device as defined in claim 1, wherein the replaceable tube has a first wall thickness adjacent a storage position of the tube, and a second wall thickness in a bending portion of the tube, wherein the second wall thickness is greater than the first wall thickness.

* * * * *